United States Patent
Triva (10) Patent No.: US 9,428,788 B2
(45) Date of Patent: Aug. 30, 2016

(54) METHOD FOR QUANTITATIVE TRANSFER OF ANALYTES

(71) Applicant: Copan Italia S.p.A., Brescia (IT)

(72) Inventor: Daniele Triva, Bovezzo (IT)

(73) Assignee: COPAN Italia S.p.A., Brescia (IT)

( * ) Notice: Subject to any disclaimer, the term of this patent is extended or adjusted under 35 U.S.C. 154(b) by 0 days.

(21) Appl. No.: 14/106,195

(22) Filed: Dec. 13, 2013

(65) Prior Publication Data

US 2014/0106445 A1 Apr. 17, 2014

Related U.S. Application Data

(63) Continuation of application No. 12/840,087, filed on Jul. 20, 2010, now Pat. No. 8,631,715.

(30) Foreign Application Priority Data

Jun. 9, 2010 (IT) .............................. MI2010A1032

(51) Int. Cl.
*C12Q 1/24* (2006.01)
*G01N 1/10* (2006.01)
(Continued)

(52) U.S. Cl.
CPC ................. *C12Q 1/24* (2013.01); *A61B 10/02* (2013.01); *B01L 3/5029* (2013.01); *G01N 1/02* (2013.01);
(Continued)

(58) Field of Classification Search
CPC .... Y10T 436/2575; G01N 1/02; G01N 1/10; G01N 2001/028; G01N 2001/2893; C12Q 1/24; B01L 2300/161; B01L 3/5029; A61B 10/02; A61B 2010/0216

USPC ............. 73/1.02, 1.03, 864.71; 600/572, 573
See application file for complete search history.

(56) References Cited

U.S. PATENT DOCUMENTS 3,163,160 A 12/1964 Cohen
3,434,801 A 3/1969 Scherr
(Continued)

FOREIGN PATENT DOCUMENTS

CN 1070850 4/1993
CN 2183735 11/1994
(Continued)

OTHER PUBLICATIONS

"Flock 2003" Int. Flock Symposium, Apr. 2003, Dresden (3 pages).
(Continued)

*Primary Examiner* — Peter Macchiarolo
*Assistant Examiner* — Natalie Huls
(74) *Attorney, Agent, or Firm* — Fish & Richardson P.C.

(57) ABSTRACT

A method for transferring a quantity of analytes comprising at least stages of: predisposing a substantially homogeneous mixture of a predetermined initial quantity of at least an analyte and a liquid, obtaining a known concentration value or known amount of the analyte in the mixture; introducing into the mixture at least a collecting portion (3) of a sampling device (1) having a support body (2), the collecting portion (3) comprising a plurality of fibers (6) attached to and arranged on a first portion (2a) of the support body (2) by means of flocking, in order to define a flocked collecting portion (3) or a flocked tampon, such as to collect a part of the mixture on the collecting portion (3); and extracting the collecting portion (3) of the sampling device (1) of the mixture, retaining on the sampling portion (3) a predetermined known quantity of the mixture to be transferred.

29 Claims, 2 Drawing Sheets

(51) Int. Cl.
*A61B 10/02* (2006.01)
*B01L 3/00* (2006.01)
*G01N 1/02* (2006.01)
*G01N 1/28* (2006.01)

(52) U.S. Cl.
CPC ......... *G01N 1/10* (2013.01); *A61B 2010/0216* (2013.01); *B01L 2300/161* (2013.01); *G01N 2001/028* (2013.01); *G01N 2001/2893* (2013.01); *Y10T 436/2575* (2015.01)

(56) References Cited

U.S. PATENT DOCUMENTS

| | | | |
|---|---|---|---|
| 3,744,499 A | | 7/1973 | Wells |
| 3,792,699 A | * | 2/1974 | Tobin et al. .................. 600/572 |
| 3,854,319 A | * | 12/1974 | Burroughs et al. ............. 73/1.03 |
| 3,888,629 A | * | 6/1975 | Bagshawe ..................... 436/541 |
| 3,900,651 A | | 8/1975 | Hoppe et al. |
| 3,954,563 A | * | 5/1976 | Mennen ........................ 600/572 |
| 4,030,978 A | | 6/1977 | Abramson |
| 4,039,934 A | | 8/1977 | Ostashko et al. |
| 4,196,167 A | * | 4/1980 | Olsen ........................... 422/411 |
| 4,234,316 A | * | 11/1980 | Hevey .......................... 436/166 |
| 4,326,545 A | | 4/1982 | Motegi et al. |
| 4,340,670 A | | 7/1982 | Mennen |
| 4,421,809 A | | 12/1983 | Bish et al. |
| 4,454,109 A | | 6/1984 | Hillman |
| 4,707,450 A | | 11/1987 | Nason |
| 4,719,181 A | | 1/1988 | Schobel et al. |
| 4,749,655 A | | 6/1988 | Monthony et al. |
| 4,754,764 A | | 7/1988 | Bayne |
| 4,767,398 A | | 8/1988 | Blasius, Jr. |
| 4,861,343 A | | 8/1989 | Neunzig |
| 4,877,036 A | | 10/1989 | Saint-Amand |
| 4,877,037 A | | 10/1989 | Ko et al. |
| 4,922,936 A | | 5/1990 | Buzzi et al. |
| 4,953,560 A | * | 9/1990 | Samuels ........................ 600/572 |
| 5,009,846 A | | 4/1991 | Gavet et al. |
| 5,022,408 A | | 6/1991 | Mohajer |
| 5,091,153 A | | 2/1992 | Bachand |
| 5,163,441 A | | 11/1992 | Monthony et al. |
| 5,279,964 A | * | 1/1994 | Chrisope ..................... 435/307.1 |
| 5,538,732 A | * | 7/1996 | Smith et al. .................. 424/402 |
| 5,614,375 A | * | 3/1997 | Citri ............................ 435/29 |
| 5,623,941 A | | 4/1997 | Hedberg et al. |
| 5,627,071 A | | 5/1997 | Triva |
| 5,676,643 A | * | 10/1997 | Cann et al. .................... 604/1 |
| 5,704,388 A | | 1/1998 | Freeman |
| 5,710,041 A | * | 1/1998 | Moorman et al. ........... 435/287.6 |
| 5,738,643 A | | 4/1998 | Stredic, III |
| 5,899,622 A | | 5/1999 | Gueret |
| 5,928,176 A | | 7/1999 | Nakatani |
| 5,944,519 A | | 8/1999 | Griffiths |
| 6,010,462 A | | 1/2000 | Stoermer, III |
| 6,080,126 A | | 6/2000 | Zygmont |
| 6,232,567 B1 | | 5/2001 | Bonino et al. |
| 6,286,246 B1 | | 9/2001 | Rachal et al. |
| 6,352,513 B1 | | 3/2002 | Anderson et al. |
| 6,413,087 B1 | | 7/2002 | Petrich et al. |
| 6,420,181 B1 | | 7/2002 | Novak |
| 6,450,810 B1 | | 9/2002 | Fischer et al. |
| 6,451,607 B1 | * | 9/2002 | Lawrence et al. ............. 436/19 |
| 6,494,856 B1 | | 12/2002 | Zygmont |
| 6,503,013 B2 | * | 1/2003 | Strauss ........................ 401/123 |
| 6,676,609 B1 | | 1/2004 | Rutenberg et al. |
| 6,732,743 B1 | | 5/2004 | Bouix et al. |
| 6,881,554 B2 | | 4/2005 | DiCesare et al. |
| 6,887,681 B2 | | 5/2005 | DiCesare et al. |
| 7,022,289 B1 | | 4/2006 | Schlein et al. |
| 7,582,067 B2 | * | 9/2009 | Van Acker .................... 604/1 |
| 7,645,608 B2 | * | 1/2010 | Greene ....................... 435/286.3 |
| 8,114,027 B2 | | 2/2012 | Triva |
| 8,133,193 B2 | * | 3/2012 | Van Acker .................... 604/1 |
| 8,317,728 B2 | | 11/2012 | Triva |
| 8,772,034 B2 | * | 7/2014 | Rasch-Menges et al. ........ 436/8 |
| 2002/0001539 A1 | | 1/2002 | DiCesare et al. |
| 2002/0197738 A1 | | 12/2002 | Matsumoto et al. |
| 2003/0073932 A1 | | 4/2003 | Varey |
| 2003/0108846 A1 | | 6/2003 | Hoertsch |
| 2004/0014063 A1 | | 1/2004 | Batteux et al. |
| 2004/0078219 A1 | | 4/2004 | Kaylor et al. |
| 2004/0158188 A1 | | 8/2004 | Kauffmann et al. |
| 2004/0197730 A1 | | 10/2004 | Rowe et al. |
| 2005/0181517 A1 | | 8/2005 | Chandler et al. |
| 2005/0267395 A1 | | 12/2005 | Mangold et al. |
| 2005/0288616 A1 | | 12/2005 | Bozenbury, Jr. et al. |
| 2006/0115805 A1 | | 6/2006 | Hansen et al. |
| 2006/0142668 A1 | | 6/2006 | Triva |
| 2006/0211978 A1 | * | 9/2006 | Do ................................ 604/2 |
| 2007/0105186 A1 | * | 5/2007 | Gibson et al. ................. 435/34 |
| 2007/0208274 A1 | | 9/2007 | Ostrowski et al. |
| 2007/0275101 A1 | | 11/2007 | Lu et al. |
| 2009/0024060 A1 | | 1/2009 | Darrigrand et al. |
| 2009/0030054 A1 | * | 1/2009 | Warmington et al. ........ 514/383 |
| 2009/0030341 A1 | | 1/2009 | Kshirsagar et al. |
| 2009/0186057 A1 | * | 7/2009 | Farmer et al. ................ 424/404 |
| 2009/0325861 A1 | * | 12/2009 | Goodheart ...................... 514/8 |
| 2010/0249649 A1 | | 9/2010 | Larkin |
| 2011/0281754 A1 | | 11/2011 | Fischer et al. |
| 2012/0150088 A1 | | 6/2012 | Triva |
| 2012/0171712 A1 | * | 7/2012 | Triva ............................. 435/29 |
| 2012/0271196 A1 | | 10/2012 | Triva |
| 2013/0072817 A1 | * | 3/2013 | Triva ............................ 600/572 |
| 2013/0338535 A1 | * | 12/2013 | Triva ............................ 600/572 |

FOREIGN PATENT DOCUMENTS

| | | | |
|---|---|---|---|
| CN | 2460050 | 11/2001 | |
| CN | 2479505 | 2/2002 | |
| CN | 2554995 | 6/2003 | |
| CN | 201131761 | 10/2008 | |
| CN | 101765551 | 6/2010 | |
| CN | 201993241 | 9/2011 | |
| DE | 298 09 833 U1 | 6/1998 | |
| DE | 10246379 A1 | 4/2004 | |
| EP | 0 223 745 | 5/1987 | |
| EP | 0 244 156 B1 | 4/1990 | |
| EP | 0 643 131 A | 3/1995 | |
| EP | 0 568 556 A1 | 7/1995 | |
| EP | 0 707 836 A2 | 4/1996 | |
| EP | 1 147 746 | 10/2001 | |
| EP | 1 358 818 A1 | 11/2003 | |
| EP | 1382730 | 1/2004 | |
| EP | 1608268 | 11/2007 | |
| EP | 2395337 | 12/2011 | |
| GB | 406850 A | 3/1934 | |
| JP | 02042972 | 2/1990 | |
| JP | 05-027671 | 4/1993 | |
| JP | 10-192050 | 7/1998 | |
| JP | 2000-152817 | 6/2000 | |
| JP | 2000342591 | 12/2000 | |
| JP | 2001-346626 | 12/2001 | |
| JP | 2002067201 | 3/2002 | |
| JP | 2002539425 | 11/2002 | |
| JP | 2003004605 | 1/2003 | |
| JP | A-2004-587 | 1/2004 | |
| JP | 2007139556 | 6/2007 | |
| JP | 2007523663 | 8/2007 | |
| WO | WO 89/10724 | 11/1989 | |
| WO | WO 92/12863 | 8/1992 | |
| WO | WO 00/09984 | 2/2000 | |
| WO | WO 00/54024 | 9/2000 | |
| WO | WO 2004/086979 | 10/2004 | |
| WO | WO2004/086979 A1 * | 10/2004 | ............ A61B 10/00 |
| WO | WO 2005/013759 | 2/2005 | |
| WO | WO 2005/110316 | 11/2005 | |
| WO | WO 2007/075412 | 7/2007 | |
| WO | WO 2008/131033 | 10/2008 | |
| WO | WO 2009/018607 | 2/2009 | |
| WO | WO 2009/134509 | 11/2009 | |
| WO | WO 2009/136892 | 11/2009 | |
| WO | WO 2009/140356 | 11/2009 | |

(56) References Cited

FOREIGN PATENT DOCUMENTS

| WO | WO 2009/158403 | 12/2009 |
|---|---|---|
| WO | 2011154849 | 12/2011 |

OTHER PUBLICATIONS

BG-Information, BGI 764, p. 7, Oct. 2000, including translation from http://babelfish.yahoo.com/translate_txt, and further as a concise statement of relevance Applicant submits that the reference was cited in the European Notice of Opposition in EP 04 724 556.8.
Cotton—Facts and General Information from Swicofil, http:/lwww.swicofil.com/products/001cotton.html, Jan. 3, 2011, (9 pages).
Cotton—Wikipedia, the free encyclopedia, http://en.\wikipedia.org/wiki/Cotton, Jan. 3, 2011 (12pages).
MicroRheologics, "New Technology for Sample Collection" 2006, (2 pages).
Millipore, "Flocked Swabs" 2007, (2 pages).
Print of website http://www.flock.de/de/2_1_historie.php, believed to be Jul. 22, 2008, and including what is believed to be an English counterpart to the website printed from Print of website in English http://www.flock.de/pages/html/de/flock/sub/historie.html?lang=EN.
What is Cotton Fibre/Properties of Cotton Fiber, http://articles.textileclass.com/cotton-fibre-what-is-cotton-fibre-cotton-f, May 11, 2011, (1 page).
Wikipedia, "Cotton Swab" http//en.wikipedia.org/wiki/Cotton swab, Jun. 22, 2011 (3 pages).
Wikipedia, "Swab" http://en.wikipedia.org/wiki/Swab, Jun. 22, 2011 (1 page).
Print of Website www.swicofil.com/flock.html, believed to be Aug. 16, 2002.
File History for EP Application No. EP04724556, foreign counterpart to present application, up to Apr. 2011, 87 pages.
International Search Report (2 pages), for related international application WO 2004/086979, published Oct. 14, 2004.
International Search Report (4 pages) and Written Opinion (7 pages), for international application ITMI20101032, mailed Feb. 24, 2011.
Notice of Rejection for related Japanese patent application No. 2006-504927 (4 pages), mailed Feb. 15, 2009.
U.S. Patent Office's File for U.S. Appl. No. 10/543,873, filed Jul. 28, 2005, entitled "Swab for Collecting Biological Specimens", inventor Daniele Triva, 758 pages.
Adolescent Medicine-Google Library, http://books.google/it/books/, retrieved on Sep. 9, 2014; 3 pages.
Applied Biosystems, Benchmarking of applicators, Dec. 19, 2006, 26 pages.
Verhoeven et al. Better Detection of Staphylococcus aureus Nasal Carriage by Use of Nylon Flocked Swabs, JCM, vol. 48, No. 11, Nov. 2010; 3 pages.
Chernesky et al. Use of Flocked Swabs and a Universal Transport Medium to Enhance Molecular Detection of Chlamydia trachomastis and Neisseria gonorrhoeae; JCM, vol. 44, No. 3, Mar. 2006, 3 pages.
Clinician's Handbook of Preventive Services, US Dept. of Health and Human Services; Public Health Service, Office of Disease Prevention and Health Promotion, p. 196; 1994.
Flock Diagram (with English Translation of Diagram) Apr. 17, 1991; 6 pages.
Hedin et al., New Technique to Take Samples from Environmental Surfaces Using Flocked Nylon Swabs; Journal of Hospital Infection 75 (2010); 4 pages.
Studies on the Electrostatic Flocking (with English translation of table); 1980; 1 pages.
Puritan presentation of HydraFlock, the superior choice for specimen collection and release, 8 pages.
Moore et al. Dry Cotton or Flocked Respiratory Swabs as a Simple Collection Technique for the Molecular Detection of Respiratory Viruses Using Real-Time NASBA, JVM 153 (2008) 6 pages.
Practical Guide for General Nursing Science Part 2—p. 195; 1999, 2 pages.
Principles of Nonwovens, INDA, Association of the Nonwoven Fabrics Industry, Cotton's Unique Fiber Morphology, 1992, 11 pages.
Relationship between flock length, fineness, thinness and process ability, Table 5 with English translation; p. 194,Leipzig 1993, 2 pages.
Schenk, "Flock Trials in Laboratory With Alternating Current", International Flock Seminar, Sep. 8-10, 1980, 2 pages.
Specimen Submission Procedure for Gynecologic Cytology and HPV Testing, Dept. of Pathology, Crittenton Hospital Medical Pathology Department; 6 pages.
Chilean office action issued in Chilean Application No. 3435-12, in reference to documents submitted Apr. 16, 2013, including partial translation, 20 pages.
Daniele Triva, "Method for Quantitative Transfer of Analytes" U.S. Appl. No. 12/840,087, filed Jul. 20, 2010 (25 pages).
Gynecological Specimens-Conventional Pap Test, Rutland Regional Health Services; prepared by Joe Walker Jr.; Jun. 10, 2011; 6 pages.
Michael L. Noel, MD: Papanicolaou Smear Adequacy: The Cervical Cytobrush and Ayre Spatula Compared with the Extended-Tip Spatula; Journal of the American Board of Family Practice, vol. 2, No. 3, Jul.-Sep. 1989, 5 pages.
Wurmb-Schwardk, "Fast and Simply DNA Extraction from Saliva and Sperm Cells Obtained from the Skin or Isolated from Swabs", Elsevier—Legal Medicine, Mar. 2006, 6 pages.
"Safety Data Sheet in Accordance with Regulation 453/2010", Jun. 6, 2011, 6 pages.
Thomasma, "A39 Optimization of Touch DNA Collection Techniques Using Alternative Swabbing Solutions", Proceedings American Academy of Forensic Sciences, XP055163017, Apr. 2010, pp. 40-41, 4 pages.
Thomasma, "The Influence of Swabbing Solutions on DNA Recovery from Touch Samples", Journal of Forensic Sciences, vol. 58, No. 2, Mar. 2013, 6 pages.

* cited by examiner

METHOD FOR QUANTITATIVE TRANSFER OF ANALYTES

The present application is a continuation of U.S. patent application Ser. No. 12/840,087, filed on Jul. 20, 2010, which claims priority under 35 U.S.C. §119 to Italian Patent Application No. MI2010A001032, filed Jun. 9, 2010, the entirety of both are hereby incorporated by reference.

The present disclosure relates to a method for quantitative transfer of analytes. In certain instances, the method is applicable for example in clinical, diagnostic and in general analytical sectors, in order to enable a sampling and transferring of predetermined known quantities of analytes towards a place of use thereof for analysis or tests of various nature.

BACKGROUND

The method is specifically applicable for collection and transfer of various substances, such as for example: micro-organisms, antibodies/antigens, antimicrobial acting substances, nucleotides, antibiotics, hormones, DNA sequences, enzymes, enrichment substances or selective supplements of cultivatable terrain, and in general organic material, biological material or of biological origin or the like.

The prior art comprises very numerous applications in which known quantities of analytes must be used, such as organic or biological substances, for various analytical or diagnostic needs. For example, company programs for verifying microbiological quality include the use of standard micro-organism cultures for verification that the requisites indicated by the reference standards have been met. For this purpose, microbiological controls are performed for verifying and validating the laboratory methods and procedures, which can for example comprise controlling the effectiveness of the selective and nutritional components of soil used for microbe culture, and also for verification of the effectiveness of inactivation operations of micro-organisms, or other for other purposes.

A further known example is given by diagnostic kits which are provided with positive and negative controls of a substance to be identified and which enable control and validation of the kit itself, as well as the test procedure and preparation of the sample to be analysed. For example, in search and identification tests of a bacterium, aimed at diagnosis of present or previous infections, such in the specific case of *Staphylococcus aureus* in a test for agglutination, a positive control performed using a sample of the bacterium must provide evident agglutination, while a negative control of the same bacterium must give no agglutination within the predetermined times included in the analytical protocol.

In a further example, in research kits for food matrix inhibitors, as in the specific case of research for antimicrobials in a milk test, a positive control performed using a solution containing an antibiotic must provide a positive result in the set times and in accordance with the test procedures.

Normally, positive controls are supplied in liquid form or freeze-dried in pellets, or powder to be re-hydrated before use, as the limited stability of rehydrated positive controls limits working life thereof significantly. Further, quantitative release in the case of controls supplied on a support is generally limited, so to obtain a positive test response, there is a general tendency to use an excess of control sample of the substance to be researched such as to exceed the quantitative threshold for each test.

As is known in the field of microbial resistance tests, after isolating the micro-organism it is necessary to determine which substance can combat the micro-organism, and in which concentration. Normally these tests are carried out by preparing a series of serial dilutions starting from a known matrix solution. The procedure for preparing the dilutions is laborious and therefore has negative economic effect on productivity of the processes carried out in the analytical laboratory. The collecting and transfer devices of known type generally used in laboratories are constituted for example by Pasteur pipettes, syringes, pads or spoons.

In all the above-cited examples, and in general in all analyte transfer methodologies and following analysis thereof, there are numerous problem areas. These problem areas are linked for example to the complexity of the preparation procedures of the analytes and the difficulties in transferring and conserving them. Note that many analytes require, for their conservation over time, very specific and controlled environmental conditions. Also the correct quantification of analytes is often complex, especially in a case of use of very small quantities of analytes, as the only way for obtaining the desired small quantity consists in preparing an analyte solution when needed having a known concentration and in directly removing a part of the solution immediately after having prepared it.

Often long, complex and expensive operations are required in order to be able to perform analysis. Further, various known analytic methodologies require the use of extremely precise quantities of analyte, for the performance of comparative tests or other analyses, and this is often difficult to obtain, if not with delicate and laborious operations. In other words, with the prior art it is not possible to avail of various types of analyte each time there is a need there for, in the quantities and specific modes suitable for the required application.

SUMMARY

In certain instances, the concepts described herein provide a method for transferring quantities of analytes which enables a sample to be obtained as well as a quantitatively-correct and precise transfer of analytes.

In certain instances, the concepts described herein provide a method for quantitative transfer of analytes which is also very efficient for analytes which are difficult to collect, transfer, conserve or treat.

In certain instances, the concepts described herein make available a method for quantitative transfer of analytes which reduces the risk of contaminations on the part of the users.

In certain instances, the concepts described herein make available a method for quantitative transfer of analytes which is applicable and effective with a broad range of analytes.

In certain instances, the concepts described herein make available a method for quantitative transfer of analytes which provides analytes that are ready for use in analytic or diagnostic tests, also in quantities which are very small and precise.

In certain instances, the concepts described herein make available a method for quantitative transfer of analytes which enables a pre-dosed sampling device to be realised of a known predetermined quantity of analyte and/or for any quantity, even a very small quantity, of analyte and/or in which the method is realisable for a broad range of analytes and/or in which the pre-dosed device exhibits analytes in a rapid-use condition.

In certain instances, the concepts described herein make available a method for quantitative analyte transfer which enables significant reduction of the complexity, the time and the costs involved in the performance of a broad range of diagnostic analyses and tests.

In certain instances, the concepts described herein make available a method for quantitative analyte transfer which is simple and economical to use.

These aims and others besides, which will more fully emerge from the following description, are substantially attained by a method for quantitative transfer of analytes as set out in one or more of the accompanying claims, taken one by one or in combination, or in any combination with one or more of the described characteristics.

In certain instances, the concepts described herein also relate to a method according to one or more of the appended method claims, wherein a stage of making a mixture substantially homogeneous is performed by vortexisation and/or by agitation using a shaker device.

In certain instances, the concepts described herein also relate to a method according to one or more of the appended method claims, further comprising the stage of realising a pre-dosed device provided with a predetermined known quantity of analyte.

In certain instances, the concepts described herein further relate to a method of one or more of the appended method claims, wherein the stages of inserting at least a collecting portion and extracting the collecting portion are manually performed by an operator and/or in which the method further comprises at least a stage of extracting the sterile device from a sealed and sterile pack before inserting the collecting portion in the mixture.

In certain instances, the concepts described herein further relate to a method of one or more of the appended method claims, in which the stage of inserting a collecting portion of the mixture is performed by direct immersion of the collecting portion in at least a micro-container or by means of a pump for micro-volumes.

In certain instances, the concepts described herein further relate to use of a device, as in one or more of the appended method claims, for performing stages of a method as in the claims below.

By way of non-limiting example, a detailed description will now follow.

DETAILED DESCRIPTION

Figure 1:
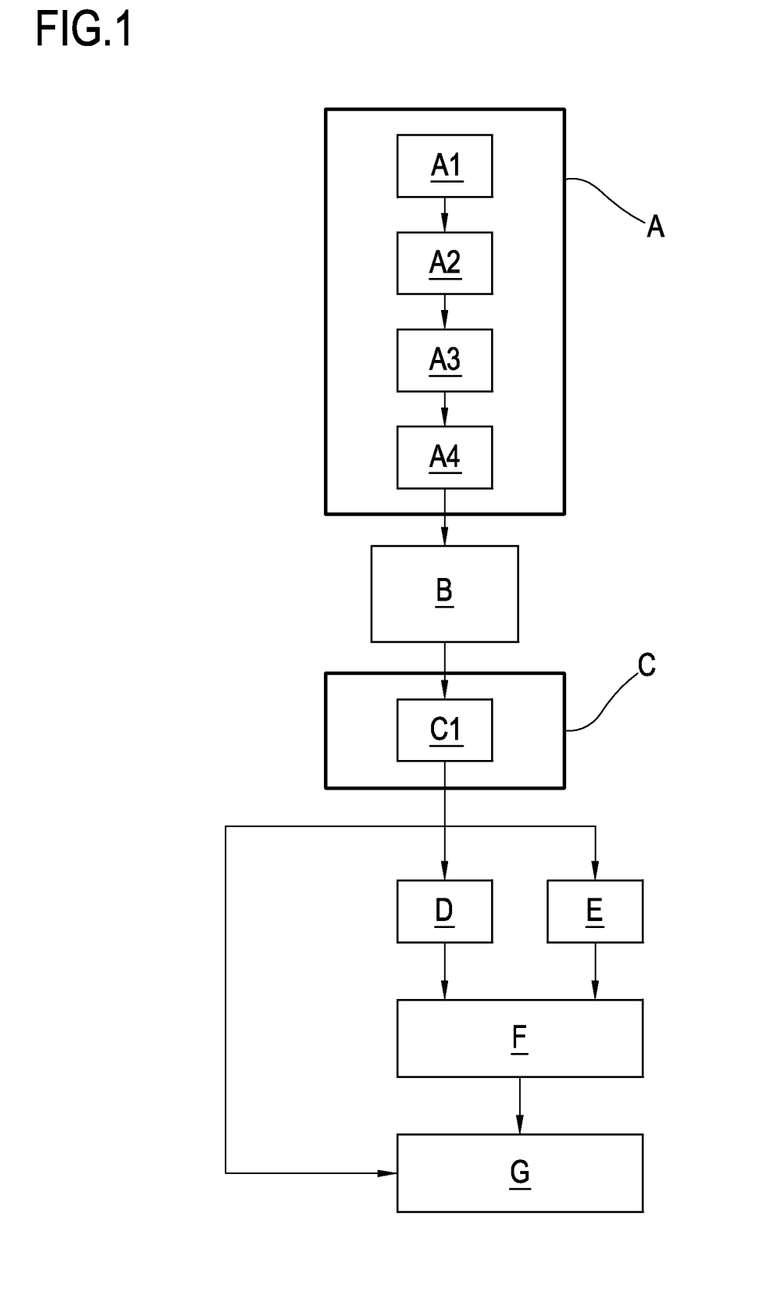
FIG. 1 is a flow diagram schematically illustrated some embodiments of a method in accordance with the concepts described herein.
Figure 2:
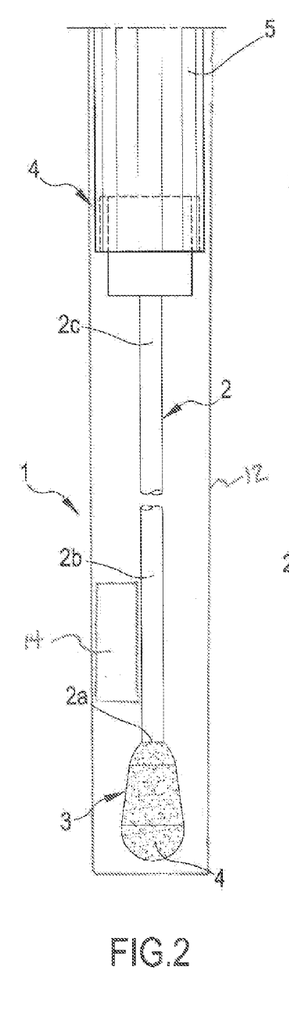
FIG. 2 is a lateral view of a device according to an embodiment in accordance with the concepts described herein.
Figure 2A:
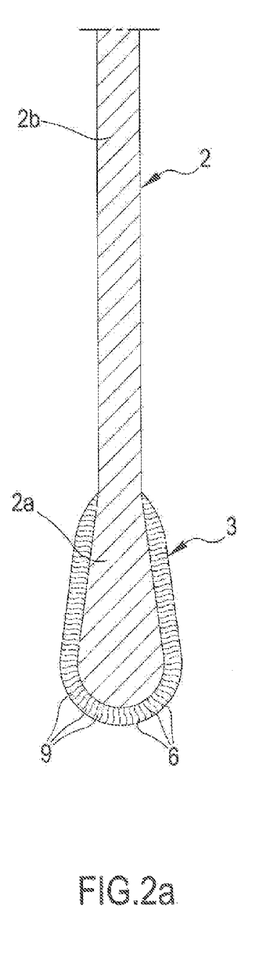
FIG. 2a is a view of a detail of the device of FIG. 2, relating to a collecting portion.

FIG. 1 illustrates a method for quantitative transfer of analytes, which comprises at least stages of predisposing (stage A in FIG. 1) a substantially homogeneous mixture, of at least a predetermined initial quantity of at least an analyte and a liquid; obtaining (stage A4) at least a known concentration of the analyte in the mixture; inserting (stage B) at least a collecting portion 3 of a sampling device 1 (see, e.g., FIG. 2) having a support body 2 in the mixture, the collecting portion 3 comprising a first portion 2a of the support body 2 and a plurality of fibres 6 (see, e.g., FIG. 2a) attached and arranged on the first portion 2a of the support body 2 by flocking, in order to define a flocked collecting portion 3, or a flocked pad, such as to collect a part of the mixture on the collecting portion 3.

In the present description, the expression "substantially homogeneous" relates to mixtures commonly defined as homogeneous, in which the components are no longer distinguishable and are in a single phase (for example solutions), and also types of mixtures generally considered heterogeneous, but which in any case exhibit, at macroscopic level, a high level of reciprocal mixing which precludes a macroscopic distinction of the various components. For example, "substantially homogeneous" is used to refer to each substance which is substantially constant in sufficiently small quantities, even if this is obtained only for a limited period of time thanks to a deliberate stage of mixing of the components of the mixtures. In other words, "substantially homogeneous" might relate to a mixture between an analyte and a liquid in which it is possible to determine, with a sufficient degree of precision, the quantity of analyte contained in a determined quantity of samplable mixture contained in a determined quantity of mixture which can be collected by the collecting portion 3 of the sampling device 1, in order to determine the quantity of analyte collected. The mixture can be saturated or not, and can also exhibit a bottom residue, as the part of the substantially homogeneous mixture of interest is the one in which the desired concentration is definable and substantially uniform in various zones of the mixture.

The method further comprises a stage of extracting (stage C in FIG. 1) the collecting portion 3 of the sampling device 1 from the mixture, while retaining, on the collecting portion 3, a predetermined known quantity to be transferred of the mixture. The concepts described herein can be aimed at transferring analytes such as for example micro-organisms, antibodies/antigens, anti-microbial substances, nucleotides, antibiotics, hormones, DNA sequences, enzymes, organic materials, biological materials or materials of biological origin, enriching supplements or selective supplements of cultivating terrain, or the like. The stage of predisposing the mixture can comprise sub-stages of predisposing (stage A1) the predetermined initial quantity of analyte; mixing (stage A2) the predetermined initial quantity of analyte with the liquid in order to obtain a mixture of the predetermined initial quantity of analyte and liquid, and/or a stage of rendering the mixture substantially homogeneous (stage A3), for example by vortexing and/or by shaking using a shaker device. The mixture can be predisposed for example in a suitable container. The stage of obtaining a known concentration value of the analyte in the mixture can be performed by mixing a known quantity of the analyte with a known quantity of the liquid and/or via the stage of measuring a concentration value of the analyte in the mixture.

The method can further comprise a stage of measuring (stage C1) the quantity of mixture effectively retained in the collecting portion 3 during the stage of extracting the collecting portion 3 of the sampling device from the mixture. The stage of measuring can be performed by means of a comparison between the initial weight of the mixture before inserting the collecting portion 3 and the final weight of the mixture after extraction of the collecting portion 3, or by a comparison between the weight of the sampling device 1 before insertion of the mixture and the weight of the sampling device 1 after extraction from the mixture.

The method can further comprise a stage of dehydrating, drying (stage D) or freeze-drying (stage E) at least the collecting portion 3, provided with the predetermined quantity of mixture to be transferred, in order to obtain a pre-dosed sampling device 1 having a predetermined quantity of dried or freeze-dried analyte on the collecting portion 3. The stage of drying can be performed, for example, by drying in an oven or by forced ventilation, or using another method of known type and suitable for treating the specific analyte. The pre-dosed sampling device 1 comprises a support body 2 and a flocked collecting portion 3 provided with a predetermined known quantity of an analyte to be transferred and/or a predetermined and dried known quantity of an analyte to be transferred.

The method can also comprise stages of inserting the collecting portion 3 in a vacuum container (of known type and therefore not illustrated in the figures) and generating a depression or vacuum in the container. This stage of generating a depression or vacuum can be performed during the stage of drying or freeze-drying, or in another moment, separately from the stage of drying or freeze-drying.

The method can further comprise a stage of revitalising or re-hydrating (stage F) the predetermined quantity of dried or freeze-dried analyte on the collecting portion 3, for example with at least a nutritional and/or hydrating solution, in order to obtain a predetermined quantity of rehydrated analyte on the collecting portion 3.

The method can further comprise a stage of releasing (stage G) at least 85% of the predetermined quantity to be transferred of the mixture or the predetermined analyte quantity, by means of direct seeding on a dish, or dilution in a liquid terrain in order to enable performing analysis on the analyte. The method can also comprise one or more stages of analysis of the analyte thus released.

Figure 3:
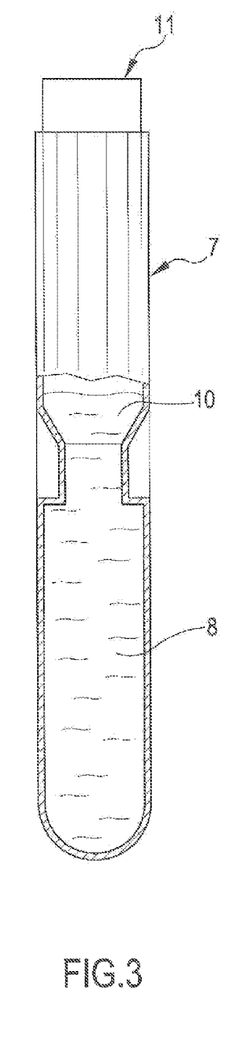
FIG. 3 is a container of an embodiment in accordance with the concepts described herein.

The method can further comprise stages of inserting the collecting portion 3, provided with the analyte, in a container 7 (see, e.g., FIG. 3) such as for example a test tube, closing the container 7 with a cap 5 or closing cover and transferring the container 7 comprising the collecting portion 3 and/or the stage of predisposing, in the container 7, a predetermined quantity of a substance 8 destined to liquefy and/or conserve the analyte and/or a stage of agitating, shaking or rotating the container 7 comprising the collecting portion 3 with the analyte at a predetermined velocity and destined to liquefy the analyte.

There now follows a description of a sampling device 1 which serves also for transferring a quantity of analyte.

With reference to the figures of the drawings, 1 denotes in its entirety a manual device 1 for sampling and transferring quantities of analytes of various nature and composition. The sampling device 1 comprises a support body 2 which can be elongate and/or substantially rod-shaped. The support body 2 can have any section, which can even be variable along the longitudinal extension thereof. The support body 2 is provided with a first portion 2a, for example an end portion, defining a collecting portion 3 for the analyte, a second portion 2b which is central and substantially rod-shaped, and a third portion 23c which is an end portion at which the body 2 can be manually gripped by an operator or which is connectable to a further gripping element 4 such as a cover 5 for a test tube or the like.

The collecting portion 3 for the analyte can be conformed as a pad. The collecting portion 3 is flocked, realised by flocking of a plurality of fibres 6 on the first end 2a of the body. The fibres 6 flocked on the first end can be made of a non-hydrophilous material, for example nylon, but the collecting portion 3 is hydrophilous by effect of capillarity thanks to the characteristics of the fibres 6 and the distribution thereof on the support body 2. In other terms, the collecting portion 3 can exhibit a continuous layer of fibres 6 made of a substantially non-absorbent material of the analyte, but conformed in an orderly plurality of capillary interstices 9 in which a predetermined quantity of the analyte can be retained by imbibing, and from which the quantity of analyte can subsequently be released quantitatively at the moment of analysis, for example by rubbing the collecting portion 3 on a special releasing surface.

An example of this type of flocked pad is illustrated in patent EP.1,608,268 belonging to the same Applicant, the content of which in the structure of the flocked pad is incorporated for purposes of reference in the present description.

As described in the above-cited patent, depositing by flocking produces, on the involved end of the sampling device 1, a continuous and homogeneous layer of a plurality of fibres 6 in an ordered arranged, substantially perpendicular in each point of the first portion 2a of the support body 2 and each of which being substantially parallel to the adjacent fibres 6. A corresponding ordered plurality of capillary interstices 9 is defined between the fibres 6, in which interstices 9 a predetermined quantity of the analyte can be collected and retained by imbibing due to capillarity.

The flocked layer can subsequently quantitatively release the collected analyte, for example by rubbing on a surface or by means of dilution of the analyte in a dilutant. The flocked collecting portion 3 is configured and dimensioned such as to collect a substantially known quantity of analyte and/or mixture, or to collect a quantity of mixture comprised, for example, between 5 and 1000 microlitres, 10 microlitres and 500 microlitres, or between 50 and 200 microlitres, or between 80 and 120 microlitres.

The fibres 6 can be arranged on the support body 2 in a substantially ordered way and such as to form a substantially continuous layer on the collecting portion 3 and/or are arranged on the collecting portion 3 such as define a plurality of capillary interstices 9 destined to absorb the mixture by capillarity. The fibres have a linear density or fibre count between 1.7 and 3.3 Dtex, and/or have a length comprised between 0.6 and 3 mm. The fibres 6 can be flocked on the collecting portion 3 of the support body 2 with a surface density for example comprised between 50 and 500 fibres per $mm^2$, or between 100 and 200 fibres per $mm^2$. The layer of fibres can define an absorption capacity for example at least of 0.5 µl per $mm^2$, or at least 0.6 µl per $mm^2$, or at least 0.7 µl per $mm^2$, or at least 0.75 µl per $mm^2$. The fibres 6 can be made of a substantially non-hydrophilic material, or a material which does not adsorb the mixture or the analyte, and/or of a material selected from among: polyamide, rayon, polyester, carbon fiber, alginate, a natural material which is non-adsorbent with regard to the mixture, or a mixture of the above materials.

The support body 2 can exhibit a longitudinal extension which is comprised between 2 cm and 20 cm, or between 3 cm and 18 cm, or between 6 cm and 16 cm and/or a thickness or diameter in a perpendicular section to the central axis thereof which is comprised between 0.5 mm and 5 mm, or between 1 mm and 3 mm, or between 1.5 and 2.5 mm.

The collecting portion 3 can exhibit a longitudinal extension which is comprised between 8 cm and 0.5 cm, or between 5 cm and 1 cm and/or a diameter or thickness, comprising the fibers 6, between 10 mm and 1 mm or between 8 mm and 2 mm or between 5 mm and 2.5 mm.

The collecting portion 3 can exhibit any suitable shape for the specific type of analyte to be sampled, for example rounded or with one or more live edges.

The support body 2 can be provided with an intermediate weakening portion destined to facilitate a selective breakage of the body 2 in an intermediate position thereof between the first end and the second end, for example in order to facilitate insertion of the collecting portion 3 into a container 7 for transport.

The sampling device 1 can comprise a plurality of support bodies, each provided with a collecting portion 3 having a conformation or shape which is different and specifically configured for collecting a specific type of analyte, or for collecting a specific quantity of analyte. The sampling device 1 can further comprise a container 7 for transport of the analyte having an internal containment seating 10 and an access opening 11. The container 7 can be a test tube for transport of samples of biological material or material of biological origin. The sampling device 1 can further comprise a closing cap 5 which is removably mountable to the opening access in order to selectively close the container 7.

The sampling device 1 can further comprise at least a drying or de-humidifying element, for example a bag containing silicon gel 14, housed in the container 7 or in another useful position. The container 7 and/or the closing cap 5 and/or the support body 2 can be realized in a plastic material, for example polystyrol or polystyrene or polypropylene and/or in a material suitable for use with biological materials or materials of biological origin. The container 7 and/or the closing cap 5 and/or the support body 2 can be sterilized.

The sampling device 1 can further comprise a sealed pack 12 ( as of known type) in which the support body 2 and/or the container 7 and the closing cap 5 can be housed before use for collecting an analyte. The support body 2, the pack 12, the container 7 and the cap 5 can be sterile.

The concepts herein further enable realizing a kit for performing diagnostic or chemical tests, such as positive or negative controls, or for transferring fragile substances in water medium for cultivating terrain supplement, comprising at least a sampling device 1 of the above-described type, and further comprising means for drying or freeze-drying a predetermined quantity of mixture on a collecting portion 3 of the sampling device 1 and/or means for revitalizing a predetermined quantity of dried or freeze-dried analyte or on the collecting portion 3 of the sampling device 1, such as for example test tubes containing nutritional and/or hydrating solutions.

As previously mentioned, in certain instances the concepts herein make it possible to design and realized pre-dosed devices for transferring analytes with substantially complete release of the analyte collected at the desired moment of use, the amount of usable analyte being at least 85% of the collected sample analyte.

The pre-dosed devices are applicable to various uses, among which the fields of diagnosis, chemistry, pharmaceutical, cosmetics, food, water control, etc. Among the analytes which can be sampled and thereafter made available for laboratory use, the following can be mentioned by way of example:

analytes of a biological and microbiological nature, such as for example micro-organisms, antibodies, antigens, hormonally-acting substances, oligo-nucleotides or sequences of DNA, enzymes, etc;

analytes of a chemical nature, such as for example antibiotics, enrichment supplements comprising proteins, selective supplements, etc.

For a better comprehension of the concepts herein, some specific but non-limiting examples are given of practical actuation, with reference to an embodiment constituted by a pad on an end of which a layer of fibers 6 is deposited, such as for example nylon fibers, by flocking. A further application is the transfer of organic material coming from various body or environmental areas. Further, purely by way of non-limiting illustration, a table is presented in which some fields of application of the pre-dosed system are summarised, in relation to the substance to be examined in the respective tests.

| Field of Application | Substance |
|---|---|
| Quality control | Micro-organisms |
|  | Antibodies/antigens |
|  | Antibiotics |
|  | Hormones |
|  | Sequences of DNA |
|  | Enzymes |
| Sensitivity tests | Antibiotics |
| Cultivating terrains | Enriching supplements |
|  | Selective supplements |

EXAMPLE 1

In a first example, the concepts herein are applied to a transfer of a quantity of living and stabilized microbes, for example for realization of a quality control kit in the microbiological field. A pre-dosed sampling device is realized for transfer of living micro-organisms which following a suitable de-hydrating process enables conservation and transport of living and stable microbe populations; at the same time the sampling device 1, in the form of a pad, provides a suitable system for direct seeding of the analyte sample on a dish or solid substrate or for dilution in a solvent or in liquid terrain.

The kit comprises a flocked pad on which, via an imbibing and subsequent freeze-drying process, a determined microbe colony at a known concentration is collected. The application field of these devices covers various clinical and food areas. The kit includes means for revitalizing the freeze-dried colony, i.e. test tubes containing nutritional and/or hydrating solutions.

A specific example will now be described, relating to *Escherichia Coli* ATCC 25922. Similar results however can be obtained with other micro-organisms.

In the present example, the pre-dosed flocked pads of freeze-dried micro-organisms are realized in a quantitative form: about 300 UFC of *Escherichia Coli* are transferred onto the pad, subjected to a freeze-drying process and then recuperated at the end of the drying process. The pre-dosed devices of freeze-dried micro-organisms can be used as reference standards in microbiological quality control in various fields, such as for example the pharmaceutical industry, in water and waste water testing, in the food industry, the cosmetic industry, and others besides.

An essential requisite for realizing these device for guaranteeing standardization of the analytical methods is that the release of the sample deposited on the collecting portion 3 of the sampling device 1 must be completely released during use. In order to realize pre-dosed sampling devices 1, the flocked collecting portion 3 is imbibed by using a microbial solution at known concentration such as to guarantee that a total quantity of about 300 UFC is transferred onto each pad. The quantity of microbial injection to be used, in the particular case of the pad, can be comprised in a range of from 10 to 200 µL and in the specific case 100 µL. The concentration of the microbial suspension used is about 3000 UFC/mL; the microbial suspension at the desired concentration is directly realized in the conservation means which contains cryo-protective substances and neutralizing agents which are able to conserve the vitality of the cells. The injection of the pads with the microbial suspension is achieved by direct immersion in micro wells; similarly a micro-volume pump can be used. The pad is inserted into a suitable depression container which can support depression technology and freeze-drying, which is dehydration, and at the end of the process it is sealed directly in a state of depression.

The tests performed for qualifying the sampling device 1 for known-quantity transfer relate to verifying of the recuperation of the deposited colonies, the vitality and stability over time under different conservation conditions. The tests were performed directly by seeding on solid terrain or by solution in a known volume, specifically 500 µL of hydrating substance. The comparison for verification of the transfer was performed using a same seeding of the sample collected using a micro-pipette.

The following table reports the mean values of the counts performed by direct seeding on solid terrain of the pre-dosed pads with *Escherichia Coli*, compared with similar results obtained using a conventional volumetric method for the transfer of the microbial suspension, such as the micro-pipette. The data relate to a sample of 50 pre-dosed pads.

| Type | Count with micropipette | Count of pre-dosed pad | Range (min-max) | Mean recuperation % |
|------|------------------------|------------------------|-----------------|---------------------|
| E. coli | 297.8 | 285.8 | 293-279 | 96% |

The table reports the mean values of the counts performed by dilution of the pre-dosed pad in 500 µL of PBS and seeding on solid terrain of the whole sample thus reconstituted with similar results obtained using, for the transfer of the microbial suspension, a conventional volumetric method such as the micro-pipette. The data refers to a sample of 50 pre-dosed pads.

| Type | Count with micropipette | Count of pre-dosed pad | Range (min-max) | Mean recuperation % |
|------|------------------------|------------------------|-----------------|---------------------|
| E. coli | 297.8 | 288.1 | 290-286 | 97% |

The flocked pad has been shown to be an excellent quantity-transfer device for maintaining the microbe colonies by a freeze-drying process. The reproducibility of the system is good, as is its stability over time.

EXAMPLE 2

In a second example, the sampling device 1 is comprised in a quality control kit in lateral flow diagnostic systems of the immune-enzymatic type, such as kits for influenza, Strep A, MRSA, HIV, RSV, and the like. In the particular case the sample device 1 is used for transfer of antigens/antibodies which following a dehydration process enables conservation and stabilization of the analyte. The pre-dosed system with the quantity of analyte modulated according to the LOD (limit of detection, or cut-off) of the specific test provides a positive control usable in the reference diagnostic kit.

The kit comprises a flocked pad on which a determined antigen or antibody at a known concentration is placed by an imbibing and subsequent drying process. The field of application of these devices covers various clinical and pharmaceutical ambits. The kit includes means which enable the test to be completed. These are devices loaded with antigens or antibodies that the kit is sensitive to (in the case of positive controls) or with no antigen/antibody or with antigens/antibodies that are different from the targets of the kit (in the case of negative controls).

Further, these controls have the aim of illustrating, to the final user, how the positive and negative results of the test should present. The sampling device 1 provided with a continuous layer of polymer composition enables interaction of an adsorbent type with the transferred analytes, guaranteeing complete collection of the analyte by the solvent means without absorption internally of the layer. This surface-interacting mechanism is a guarantee of the complete release of the analyte during use.

EXAMPLE 3

In a third example, the sampling device 1 is comprised in a quality control kit for research for inhibiting substances in milk and derivatives; similar applications are also possible for other food matrices. In this case the sampling device 1 is for the transfer of anti-microbial substances which successively enables a suitable dehydrating system for dehydrating to conserve the analyte. The pre-dosed system with a predefined quantity of anti-microbe substance provides, after rehydration, a positive control for the reference test in the milk sample. The kit comprises a flocked pad to which, by a drying process, a determined antibiotic with a known concentration is adhered. The kit includes means which enable the test to be performed. These are devices loaded with antibiotics to which the kit is sensitive (in the case of positive controls) or without any antibiotic or with antibiotics that are different from the kit's targets (in the case of negative controls). Further, these controls have the aim of illustrating, for the benefit of the final user, how the positive and negative result of the test should be presented.

EXAMPLE 4

In a fourth example, the sampling device 1 is comprised in a kit for verifying the resistance to antibiotics of determined micro-organisms (MIC, minimum concentration inhibitor). In this case the sampling device 1 for the transfer of antimicrobial substances subsequently enables an appropriate system for dehydration to stabilize the deposited antibiotics and make them available in tests for microbic resistance. The kit comprises a series of flocked pads on which, via a process of imbibing and drying, a determined different quantity is adhered of anti-microbe substance of known concentration. The field of application of these devices covers various clinical and pharmaceutical fields.

EXAMPLE 5

In a fifth example, the sampling device 1 is comprised in a quality control kit with biochemical methods. In this case the sampling device 1 is for transfer of nucleotides and enables, following a suitable dehydrating process, conservation and stabilization of the analyte. The system, pre-dosed with a quantity of analyte modulated according to the cut-off of the specific test, provides a positive control which can be used in the reference diagnostic method. The kit comprises a flocked pad on which, via a process of imbibing and subsequent drying, a determined nucleotide is adhered at a known concentration. The field of application of these devices covers various clinical and pharmaceutical ambits. The kit includes means which enable the test to be completed. These are devices loaded with nucleotides which can react with the reactives of the reference instruments, in the case of positive controls, or without nucleotides, in the case of negative controls. Further, these controls have the aim of illustrating to the final user how the positive and negative result of the test should be presented.

EXAMPLE 6

In a sixth example, the sampling device 1 is comprised in a kit for quality control in tests for detecting hormones (e.g. pregnancy tests, anti-doping, etc.) In this case the sampling device 1 is for transferring the hormones, which following a dehydration process enables conservation and stabilization of the analyte. The pre-dosed system, with a quantity of modulated analyte according to LOD (limit of detection, or cut-off) of the specific test provides a positive control usable in the reference diagnostic kit.

The kit comprises a flocked pad on which, by a process of imbibing and subsequent drying, a determined hormone at a known concentration adheres. The field of application of these devices covers various clinical and food areas.

The kit includes means which enable the test to be completed. These are devices loaded with hormones to which the kit is sensitive (in the case of positive controls), or without any hormones or with different hormones from the target hormones of the kit (in the case of negative controls). Further, these controls have the aim of illustrating to the final user how the positive and negative test results should be presented.

EXAMPLE 7

In a seventh example, the sampling device 1 is comprised in a kit for quantitative transfer of biological samples coming from various body areas, or environmental samples from surface collections. In particular the sampling device 1 is used for quantity transfer of clinical samples, such as urine, feces, bronchial washes, nostrils, vagina, pharynges, groin and other surface pads. The application relates to the control of microbial contamination of the samples.

EXAMPLE 8

In an eighth example, the sampling device 1 is used for quantity transfer of a given quantity of organic sample comprising sperm, saliva, blood. The application relates to the analysis of nucleic acids contained in the sample.

EXAMPLE 9

In a further example, the sampling device 1 comprises a kit for transfer, conservation and release of determined enrichment supplements and/or selective supplements for cultivated terrain. The sampling device 1 for quantitative transfer of substances for increasing the fertility of cultivating terrain (for example amino acids, sugars, proteins, etc.) or which enable growth of determined micro-organisms while preventing growth of others (such as for example salts, antibiotics, chemical substances, etc.) when specially imbibed and dehydrated enables a pre-dosed system to be obtained which is directly usable in the correct volume of liquid terrain.

Many of the substances used for enriching cultivating terrain have a limited stability in the hydrated state; this limits and compromises the use of the terrain itself. The advantage of a pre-dosed sampling device 1 is that the system is available and ready to use, enabling a lengthening of the useful life of the cultivating terrain by simplifying management of the measures to be taken and the conservation of the terrain itself. The field of application of these devices covers various clinical, food and pharmaceutical areas.

Certain instances of the concepts described herein provide one or more, or none, of the following advantages.

In certain instances, the concepts described herein enable realization of a method and a device realized in accordance with the method, which obviates the problems encountered in the prior art. In certain instances, the concepts described herein leads to obtaining a sample and a transfer which are quantitatively correct and precise, of various types of analyte, and in a very efficient way, even with analytes that are difficult to sample, transfer, conserve or treat.

Further, in certain instances, the concepts described herein provide analytes that are ready for use in analytic or diagnostic examinations, in quantities that can be very small and precise, thanks to the realization of pre-dosed quantities that are ready for use.

In certain instances, the concepts described herein enable significant reductions in complexity, time and costs involved in carrying out a broad range of diagnostic analyses and tests.

In certain instances, with the concepts described herein, pre-dosed systems with different anti-microbial substances can be realized, thanks to which the subsequent injection of the micro-organisms into the growth terrain, added-to with systems pre-dosed with anti-microbials in various quantities enables an easy definition of the sensitivity and resistance of the micro-organism.

Further, in certain instances, the concepts described herein enable obtaining a quantitative positive or negative control in a form which is suitable for application in specific cases, such as to be able to correlate the response of the kit to the actual concentration of the positive control, resulting in the advantage of avoiding the use of an excessive reference sample.

In certain instances, the application of a system pre-dosed with a predefined quantity of freeze-dried micro-organisms in a format which is immediately adaptable to the application itself leads to a significant reduction in costs and times of the relative procedures.

Finally, in certain instances, the concepts described herein are simple and economic to use.

The invention claimed is:

1. A pre-dosed sampling device (1) comprising a support body (2) and a flocked collecting portion (3), the flocked collecting portion (3) including a plurality of fibers (6) attached to and arranged on a first portion (2a) of the support body (2) by flocking, wherein the flocked collecting portion (3) is provided with a dried predetermined and pre-dosed known quantity of an analyte to be transferred, wherein the flocked collecting portion (3) is configured to absorb a quantity of liquid comprised between 10 microlitres and 500 microlitres, by capillarity effect.

2. The pre-dosed sampling device (1) of claim 1 wherein the collecting portion (3) is provided with a freeze-dried predetermined known quantity of the analyte to be transferred.

3. The pre-dosed sampling device (1) of claim 2 wherein the collecting portion (3) is provided with a freeze-dried predetermined known quantity of micro-organisms to be transferred.

4. The pre-dosed sampling device (1) of claim 1 further comprising a container (7) for transport at least of the collecting portion (3) with the analyte.

5. The pre-dosed sampling device (1) of claim 4 wherein said container (7) has a containment seating (10) and an access opening (11), and further comprises a closing cap (5) which is removably mountable to the opening access in order to selectively close the container (7).

6. The pre-dosed sampling device (1) of claim 4 wherein said container (7) is a test tube for transport of samples of biological material or material of biological origin.

7. The pre-dosed sampling device (1) of claim 4 wherein the container (7) further comprises a predetermined quantity of a substance (8) to liquefy the analyte.

8. The pre-dosed sampling device (1) of claim 4 wherein the container (7) further comprises a predetermined quantity of a substance (8) to conserve the analyte.

9. The pre-dosed sampling device (1) of claim 4 further comprising at least a drying or de-humidifying element.

10. The pre-dosed sampling device (1) of claim 9 wherein said drying or de-humidifying element is a bag containing silicon gel.

11. The pre-dosed sampling device (1) of claim 4 further comprising a sealed pack wherein the container (7) is housed.

12. The pre-dosed sampling device (1) of claim 11 wherein the sealed pack is sterile.

13. The pre-dosed sampling device (1) of claim 1 wherein the flocked collecting portion (3) is configured to absorb a quantity of liquid comprised between 50 and 200 microlitres, by capillarity effect.

14. The pre-dosed sampling device (1) of claim 1 further comprising a sealed pack wherein the support body (2) is housed.

15. The pre-dosed sampling device (1) of claim 14 wherein the sealed pack is sterile.

16. The pre-dosed sampling device (1) of claim 1 wherein said analyte is micro-organisms.

17. A kit for performing diagnostic or chemical tests, the kit comprising at least a pre-dosed sampling device (1) according to claim 1.

18. A kit according to claim 17 further comprising a device for drying a predetermined quantity of mixture on a collecting portion (3) of the sampling device (1).

19. A kit according to claim 18 further comprising a device for revitalizing a predetermined quantity of dried or freeze-dried analyte on the collecting portion (3) of the sampling device (1).

20. A kit according to claim 19 wherein said device for revitalizing is a test tube containing nutrient and/or hydrating solutions.

21. A kit according to claim 19 realized for positive or negative controls, or for transferring labile substances in a hydrated phase to cultivating terrains.

22. The pre-dosed sampling device (1) of claim 1 wherein said analyte is chosen from the group consisting of: antigens, enzymes, enrichment supplements comprising proteins and selective supplements.

23. The pre-dosed sampling device (1) of claim 1 wherein said analyte is chosen from the group consisting of: antibodies, hormonally-acting substances, oligo-nucleotides or sequences of DNA.

24. The pre-dosed sampling device (1) of claim 1 wherein said analyte is antibiotics.

25. A pre-dosed sampling device (1) comprising a support body (2) and a flocked collecting portion (3), the flocked collecting portion (3) including a plurality of fibers (6) attached to and arranged on a first portion (2a) of the support body (2) by flocking, wherein the flocked collecting portion (3) is provided with a dried predetermined and pre-dosed known quantity of micro-organisms to be transferred.

26. The pre-dosed sampling device (1) of claim 25 wherein said predetermined known quantity of micro-organisms to be transferred is freeze-dried.

27. A pre-dosed sampling device (1) comprising a support body (2) and a flocked collecting portion (3), the flocked collecting portion (3) including a plurality of fibers (6) attached to and arranged on a first portion (2a) of the support body (2) by flocking, wherein the flocked collecting portion (3) is provided with a dried predetermined and pre-dosed known quantity of an analyte to be transferred, further comprising a container (7) for transport at least of the collecting portion (3) with the analyte and wherein the container (7) further comprises a predetermined quantity of a substance (8) to liquefy the analyte.

28. A pre-dosed sampling device (1) comprising a support body (2) and a flocked collecting portion (3), the flocked collecting portion (3) including a plurality of fibers (6) attached to and arranged on a first portion (2a) of the support body (2) by flocking, wherein the flocked collecting portion (3) is provided with a dried predetermined and pre-dosed known quantity of an analyte to be transferred, wherein said analyte is chosen from the group consisting of: antigens, enzymes, enrichment supplements comprising proteins and selective supplements.

29. A pre-dosed sampling device (1) comprising a support body (2) and a flocked collecting portion (3), the flocked collecting portion (3) including a plurality of fibers (6) attached to and arranged on a first portion (2a) of the support body (2) by flocking, wherein the flocked collecting portion (3) is provided with a dried predetermined and pre-dosed known quantity of an analyte to be transferred, wherein said analyte is chosen from the group consisting of: antibodies, hormonally-acting substances, oligo-nucleotides or sequences of DNA.

* * * * *